US012747456B2

(12) United States Patent
Church et al.

(10) Patent No.: US 12,747,456 B2
(45) Date of Patent: *Sep. 29, 2026

(54) MULTIPLEX RNA-GUIDED GENOME ENGINEERING

(71) Applicant: President and Fellows of Harvard College, Cambridge, MA (US)

(72) Inventors: George M. Church, Brookline, MA (US); James Dicarlo, Boston, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 19 days.

This patent is subject to a terminal disclaimer.

(21) Appl. No.: 17/837,089

(22) Filed: Jun. 10, 2022

(65) Prior Publication Data

US 2022/0380811 A1 Dec. 1, 2022

Related U.S. Application Data

(63) Continuation of application No. 14/903,719, filed as application No. PCT/US2014/045691 on Jul. 8, 2014, now Pat. No. 11,459,585.

(60) Provisional application No. 61/844,168, filed on Jul. 9, 2013.

(51) Int. Cl.
*C12N 15/00* (2006.01)
*C12N 15/11* (2006.01)
*C12N 15/90* (2006.01)

(52) U.S. Cl.
CPC .......... *C12N 15/902* (2013.01); *C12N 15/111* (2013.01); *C12N 2310/20* (2017.05)

(58) Field of Classification Search
CPC .. C12N 15/902; C12N 15/111; C12N 2310/20
See application file for complete search history.

(56) References Cited

U.S. PATENT DOCUMENTS

| | | | | |
|---|---|---|---|---|
| 2004/0171154 | A1 | 9/2004 | Storici et al. | |
| 2010/0076057 | A1 | 3/2010 | Sontheimer et al. | |
| 2013/0052646 | A1 | 2/2013 | Tripathi et al. | |
| 2014/0068797 | A1* | 3/2014 | Doudna | A61K 38/465 435/375 |
| 2014/0357530 | A1 | 12/2014 | Zhang et al. | |
| 2015/0284727 | A1 | 10/2015 | Kim et al. | |

FOREIGN PATENT DOCUMENTS

| | | | |
|---|---|---|---|
| CN | 87100610 | A | 9/1987 |
| CN | 102648282 | A | 8/2012 |
| CN | 102858985 | A | 1/2013 |
| JP | 2010-131014 | A | 6/2010 |
| JP | 2013-520989 | A | 6/2013 |
| JP | 7676351 | B2 | 5/2025 |
| WO | 00/52146 | A2 | 9/2000 |
| WO | 2013176772 | A1 | 11/2013 |
| WO | 2014/165612 | A2 | 10/2014 |

OTHER PUBLICATIONS

DiCarlo et al "Genome engineering in Saccharomyces cerevisiae using CRISPR-Cas systems" (NAR 2013 vol. 41, No. 7, published online Mar. 2013). (Year: 2013).*
Mali et al (Science vol. 339, pp. 823-826, published online Jan. 3, 2013) . (Year: 2013).*
Jinek_et_al_Jan. 29, 2013 (Year: 2013).*
The Rios Villanueva Dissertation (Harvard University, 2013) is titled: "Toward Multiplex Genome Engineering in Mammalian Cells". ( Year: 2013).*
Wang_et_al_May 2013 (Year: 2013).*
Cong_et_al Science vol. 339 published Jan. 3, 2013 (Year: 2013).*
Mali_et_al_Science_vol. 339_ppp. 823-826_published_Jan. 3, 2013 (Year: 2013).*
Mali_et_al_(Science vol. 339, pp. 823-826, published online Jan. 3, 2013 Supplementary_Information_2013 (Year: 2013).*
International Search Report issued from corresponding PCT/US2014/045691, dated Nov. 7, 2014.
Mali, P et al. RNA-Guided Human Genome Engineering via Cas9. Feb. 15, 2013; p. 1, paragrpah one to p. 1, paragraph three; p. 2, paragraph one to p. 2, paragraph four; p. 7, figure 1.
Yu, Zeta I. Highly Efficient Genome Modifications Mediated By CRISPR/Cas9 In *Drosophila*. Jul. 5, 2013. Genetics. abstract; 113.153825.
DiCarlo, J et al. Genome Engineering In Saccharomyces Cerevisiae Using CRISPR-Cas Systems. Mar. 4, 2013. Nucleic Acid Research. Nos. 1-8; abstract DOI:10.1093/nar/gkt135.
Cong et al., "Multiplex Genome Engineering Using CRISPR/Cas Systems." Feb. 15, 2013. Science. vol. 339, No. 6121; pp. 819-823. DOI: 10.1126/science.1231143.
Gratz et al.: "Genome Engineering of Drosophila with the CRISPR RNA-Guided Cas9 Nuclease", Genetics, vol. 194, No. 4, May 24, 2013 (May 24, 2013), pp. 1029-1035.
DiCarlo James E et al.: "Yeast Oligo-Mediated Genome Engineering (YOGE)," ACS Synthetic Biology, vol. 2, No. 12, Dec. 2013 (Dec. 2013), pp. 741-749.
DiCarlo James E. et al.: "Safeguarding CRISPR-Cas9 gene drives in yeast (incl. Online Methods)", Nature Biotechnology, vol. 33, No. 12, Dec. 2015 (Dec. 2015), pp. 1250-1255+2pp.
Extended European Search Report issued from corresponding EP 14822995.8, issued on Dec. 9, 2016.

(Continued)

*Primary Examiner* — Catherine S Hibbert
(74) *Attorney, Agent, or Firm* — Banner & Witcoff, Ltd.

(57) ABSTRACT

Methods of multiplex genome engineering in cells using Cas9 is provided which includes a cycle of steps of introducing into the cell a first foreign nucleic acid encoding one or more RNAs complementary to the target DNA and which guide the enzyme to the target DNA, wherein the one or more RNAs and the enzyme are members of a co-localization complex for the target DNA, and introducing into the cell a second foreign nucleic acid encoding one or more donor nucleic acid sequences, and wherein the cycle is repeated a desired number of times to multiplex DNA engineering in cells.

13 Claims, 15 Drawing Sheets

Specification includes a Sequence Listing.

(56) References Cited

OTHER PUBLICATIONS

Jiang, Wenyan et al. RNA-guided editing of bacterial genomes using CRISPR-Cas systems. Natural Biotechnol., Jan. 29, 2013. vol. 31, pp. 233-241.
Jinek, Martin et al. A Programmable Dual-RNA-Guided DNA Endonuclease in Adaptive Bacterial Immunity. Science, Aug. 12, 2012, vol. 337, pp. 816-821 and Supplementary Materials.
Japanese Office Action issued for Japanese Application No. 2016-525411 dated Sep. 4, 2018.
Jiang, Wenyan et al. RNA-guided editing of bacterial genomes using CRISPR-Cas systems. Natural Biotechnol., Jan. 29, 2013. vol. 31, pp. 233-241 and Supplementary Materials. Supplementary text: Analysis of deep sequencing data.
[Duplicate Reference] Cong, L., et al., "Multiplex Genome Engineering Using CRISPR/Cas Systems," Science, Feb. 15, 2013, vol. 339, pp. 819-823 and Supplementary Materials (document indicating a well-known technique).
Official Notification issued May 3, 2020 for IL 243475.
First Examination Report dated Feb. 24, 2020 for IN 201617001472.
Official Action and Search Report issued on May 27, 2020 for RU 2019135885.
Pougach et al., "CRISPR Adaptive Immunity Systems of Prokaryotes," Molecular Biology, vol. 46, No. 2, pp. 175-182 (2012).
Sep. 4, 2020—(NZ) First Examination Report—App. No. 716604.
Sep. 4, 2020—(NZ) First Examination Report—App. No. 754833.
Aug. 28, 2020—(KR) Notice of Preliminary Rejection—App. No. 10-2016-7003073.
Oct. 23, 2020—(RU) Office Action—App. No. 2019135885.
Jiang et al. "CRISPR-assisted editing of bacterial genomes" Nature Biotechnology, Mar. 2013; 31(3): 233-239.
Oct. 13, 2020—(AU) Notice of acceptance for patent application—Appl No. 2014287393.
Dec. 13, 2020—(KR) Notice of Final Rejection—App. No. 10-2016-7003073.
Ishikawa et al., "High efficiency gene transfer into mammalian cells by a double transfection protocol," Nucleic Acids Research, vol. 20, No. 15, p. 4367 (Jul. 3, 1992).
Mar. 25, 2021—(NZ) Second Examination Report—App. No. 754833.
Mar. 25, 2021—(NZ) Second Examination Report—App. No. 716604.
Mar. 2, 2021—(JP) Notice of Reasons for Rejection—App. No. 2019-238862.
Wang et al., "Programming cells by multiplex genome engineering and accelerated evolution," Nature, vol. 460, pp. 894-898 (2009).
Wang et al., "One-Step Generation of Mice Carrying Mutations in Multiple Genes by CRISPR/Cas-Mediated Genome Engineering," Cell, vol. 153, No. 4, pp. 910-918 (May 9, 2013).
Jul. 27, 2021—(JP) Notice of Reasons for Rejection—Ex Parte Reexam No. 2019-17787—App. No. 2016-525411.
Oct. 27, 2021—(IL) Notification of Defects—App. No. 243475.
Feb. 10, 2022—(CN) Notice on Reexamination—App. No. 201480048643.1.
Feb. 1, 2022—(JP) Notice of Reasons for Rejection—App. No. 2019-238862.
Li Fuguang et al., "Cotton Molecular Breeding," China Agricultural University Press, May 1, 2013, pp. 121-124.
DiCarlo et al., "Genome engineering in Saccharomyces cerevisiae using CRISPR-Cas systems," Nucleic Acids Research, vol. 41, No. 7, 2013, pp. 4336-4343.
Mali et al., "RNA-guided human genome engineering via Cas9," Science, vol. 339, No. 6121, pp. 823-826.
Ke Xie et al., "Research Progress of Genome Editing in Plants," China Biotechnology, vol. 33, No. 6, 2013, pp. 99-104.

* cited by examiner

RNA guided Genome cleavage via Cas9

Allele Replacement using oligonucleotides targeting four loci crucial in thermotolerance in yeast

FIG. 5A

Thermotolerance to heat shock in select mutants

| Strain | Code |
|---|---|
| Wild-Type | WT |
| ras2 | B1 |
| sch9 | B2 |
| ubc1(S97A) | B3 |
| tfs1 | B4 |
| sch9 tfs1 | C2 |
| ras2 tfs1 | C4 |
| sch9 ubc1 (S97A) | C5 |
| tfs1 ubc1 (S97A) | C6 |
| ras2 tfs1 ubc1 (S97A) | D3 |

MULTIPLEX RNA-GUIDED GENOME ENGINEERING

RELATED APPLICATION DATA

This application is a continuation application which claims priority to U.S. patent application Ser. No. 14/903,719, filed on Jan. 8, 2016 is a National Stage Application under 35 U.S.C. 371 of co-pending PCT Application No. PCT/US14/45691 designating the United States and filed Jul. 8, 2014; which claims the benefit of U.S. Provisional Patent Application No. 61/844,168 filed on Jul. 9, 2013 each of which are hereby incorporated by reference in their entireties.

STATEMENT OF GOVERNMENT INTERESTS

This invention was made with government support under DE-FG02-02ER63445 awarded by U.S. Department of Energy, and under 0540879 awarded by National Science Foundation. The government has certain rights in the invention.

SEQUENCE LISTING

The instant application contains a Sequence Listing which has been submitted electronically in ASCII format and is hereby incorporated by reference in its entirety. Said ASCII copy, created on Jun. 5, 2017, is named 010498_00692-US_SL.txt and is 12,600 bytes in size.

BACKGROUND

Bacterial and archaeal CRISPR-Cas systems rely on short guide RNAs in complex with Cas proteins to direct degradation of complementary sequences present within invading foreign nucleic acid. See Deltcheva, E. et al. CRISPR RNA maturation by trans-encoded small RNA and host factor RNase III. Nature 471, 602-607 (2011); Gasiunas, G, Barrangou, R., Horvath, P. & Siksnys, V. Cas9-crRNA ribonucleoprotein complex mediates specific DNA cleavage for adaptive immunity in bacteria. Proceedings of the National Academy of Sciences of the United States of America 109, E2579-2586 (2012); Jinek, M. et al. A programmable dual-RNA-guided DNA endonuclease in adaptive bacterial immunity. Science 337, 816-821 (2012); Sapranauskas, R. et al. The *Streptococcus thermophilus* CRISPR/Cas system provides immunity in *Escherichia coli*. Nucleic acids research 39, 9275-9282 (2011); and Bhaya, D., Davison, M. & Barrangou, R. CRISPR-Cas systems in bacteria and archaea: versatile small RNAs for adaptive defense and regulation. Annual review of genetics 45, 273-297 (2011). A recent in vitro reconstitution of the *S. pyogenes* type II CRISPR system demonstrated that crRNA ("CRISPR RNA") fused to a normally trans-encoded tracrRNA ("trans-activating CRISPR RNA") is sufficient to direct Cas9 protein to sequence-specifically cleave target DNA sequences matching the crRNA. Expressing a gRNA homologous to a target site results in Cas9 recruitment and degradation of the target DNA. See H. Deveau et al., Phage response to CRISPR-encoded resistance in *Streptococcus thermophilus*. Journal of Bacteriology 190, 1390 (February, 2008).

SUMMARY

Aspects of the present disclosure are directed to the multiplex modification of DNA in a cell using one or more guide RNAs (ribonucleic acids) to direct an enzyme having nuclease activity expressed by the cell, such as a DNA binding protein having nuclease activity, to a target location on the DNA (deoxyribonucleic acid) wherein the enzyme cuts the DNA and an exogenous donor nucleic acid is inserted into the DNA, such as by homologous recombination. Aspects of the present disclosure include cycling or repeating steps of DNA modification on a cell to create a cell having multiple modifications of DNA within the cell. Modifications may include insertion of exogenous donor nucleic acids.

Multiple exogenous nucleic acid insertions can be accomplished by a single step of introducing into a cell, which expresses the enzyme, nucleic acids encoding a plurality of RNAs and a plurality of exogenous donor nucleic acids, such as by co-transformation, wherein the RNAs are expressed and wherein each RNA in the plurality guides the enzyme to a particular site of the DNA, the enzyme cuts the DNA and one of the plurality of exogenous nucleic acids is inserted into the DNA at the cut site. According to this aspect, many alterations or modification of the DNA in the cell are created in a single cycle.

Multiple exogenous nucleic acid insertions can be accomplished in a cell by repeated steps or cycles of introducing into a cell, which expresses the enzyme, one or more nucleic acids encoding one or more RNAs or a plurality of RNAs and one or more exogenous nucleic acids or a plurality of exogenous nucleic acids wherein the RNA is expressed and guides the enzyme to a particular site of the DNA, the enzyme cuts the DNA and the exogenous nucleic acid is inserted into the DNA at the cut site, so as to result in a cell having multiple alterations or insertions of exogenous DNA into the DNA within the cell. According to one aspect, the cell expressing the enzyme can be a cell which expresses the enzyme naturally or a cell which has been genetically altered to express the enzyme such as by introducing into the cell a nucleic acid encoding the enzyme and which can be expressed by the cell. In this manner, aspects of the present disclosure include cycling the steps of introducing RNA into a cell which expresses the enzyme, introducing exogenous donor nucleic acid into the cell, expressing the RNA, forming a co-localization complex of the RNA, the enzyme and the DNA, enzymatic cutting of the DNA by the enzyme, and insertion of the donor nucleic acid into the DNA. Cycling or repeating of the above steps results in multiplexed genetic modification of a cell at multiple loci, i.e., a cell having multiple genetic modifications.

According to certain aspects, a method of increasing rate of homologous recombination is provided by the cycling method described above. In one embodiment, genomic Cas9 directed DNA cutting stimulates exogenous DNA via dramatically increasing the rate of homologous recombination. According to a certain additional aspect, the exogenous donor nucleic acid includes homology sequences or arms flanking the cut site. According to a certain additional aspect, the exogenous donor nucleic acid includes a sequence to remove the cut sequence. According to a certain additional aspect, the exogenous donor nucleic acid includes homology sequences or arms flanking the cut site and a sequence to remove the cut site. In this manner, Cas9 can be used as a negative selection against cells that do not incorporate exogenous donor DNA. Accordingly, a negative selection method is provided for identifying cells having high recombination frequency.

According to certain aspects, DNA binding proteins or enzymes within the scope of the present disclosure include a protein that forms a complex with the guide RNA and with the guide RNA guiding the complex to a double stranded DNA sequence wherein the complex binds to the DNA sequence. According to one aspect, the enzyme can be an RNA guided DNA binding protein, such as an RNA guided DNA binding protein of a Type II CRISPR System that binds to the DNA and is guided by RNA. According to one aspect, the RNA guided DNA binding protein is a Cas9 protein.

This aspect of the present disclosure may be referred to as co-localization of the RNA and DNA binding protein to or with the double stranded DNA. In this manner, a DNA binding protein-guide RNA complex may be used to cut multiple sites of the double stranded DNA so as to create a cell with multiple genetic modifications, such as multiple insertions of exogenous donor DNA.

According to certain aspects, a method of making multiple alterations to target DNA in a cell expressing an enzyme that forms a co-localization complex with RNA complementary to the target DNA and that cleaves the target DNA in a site specific manner is provided including (a) introducing into the cell a first foreign nucleic acid encoding one or more RNAs complementary to the target DNA and which guide the enzyme to the target DNA, wherein the one or more RNAs and the enzyme are members of a co-localization complex for the target DNA, introducing into the cell a second foreign nucleic acid encoding one or more donor nucleic acid sequences, wherein the one or more RNAs and the one or more donor nucleic acid sequences are expressed, wherein the one or more RNAs and the enzyme co-localize to the target DNA, the enzyme cleaves the target DNA and the donor nucleic acid is inserted into the target DNA to produce altered DNA in the cell, and repeating step (a) multiple times to produce multiple alterations to the DNA in the cell.

According to one aspect, the cell is a eukaryotic cell. According to one aspect, the cell is a yeast cell, a plant cell or an animal cell. According to one aspect, the cell is a mammalian cell.

According to one aspect, the RNA is between about 10 to about 500 nucleotides. According to one aspect, the RNA is between about 20 to about 100 nucleotides.

According to one aspect, the one or more RNAs is a guide RNA. According to one aspect, the one or more RNAs is a tracrRNA-crRNA fusion.

According to one aspect, the DNA is genomic DNA, mitochondrial DNA, viral DNA, or exogenous DNA.

Further features and advantages of certain embodiments of the present invention will become more fully apparent in the following description of embodiments and drawings thereof, and from the claims.

BRIEF DESCRIPTION OF THE DRAWINGS

The foregoing and other features and advantages of the present embodiments will be more fully understood from the following detailed description of illustrative embodiments taken in conjunction with the accompanying drawings in which:

FIG. 5A is a table of strains having mutations.

DETAILED DESCRIPTION

Figure 1:
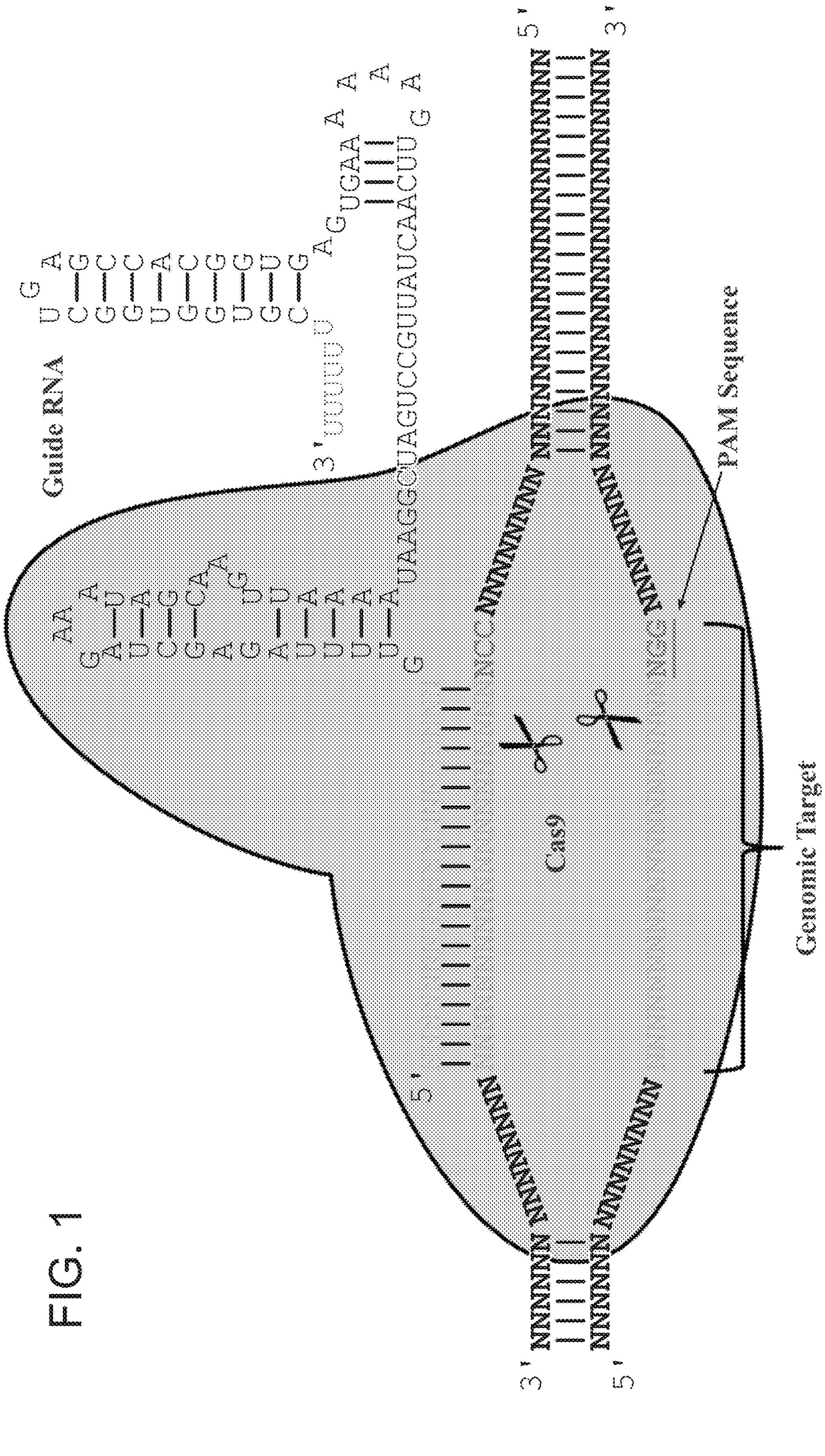
FIG. 1 is a schematic of RNA guided genome cleavage via Cas9. Guide RNA is disclosed as SEQ ID NO: 1.
Figure 1:
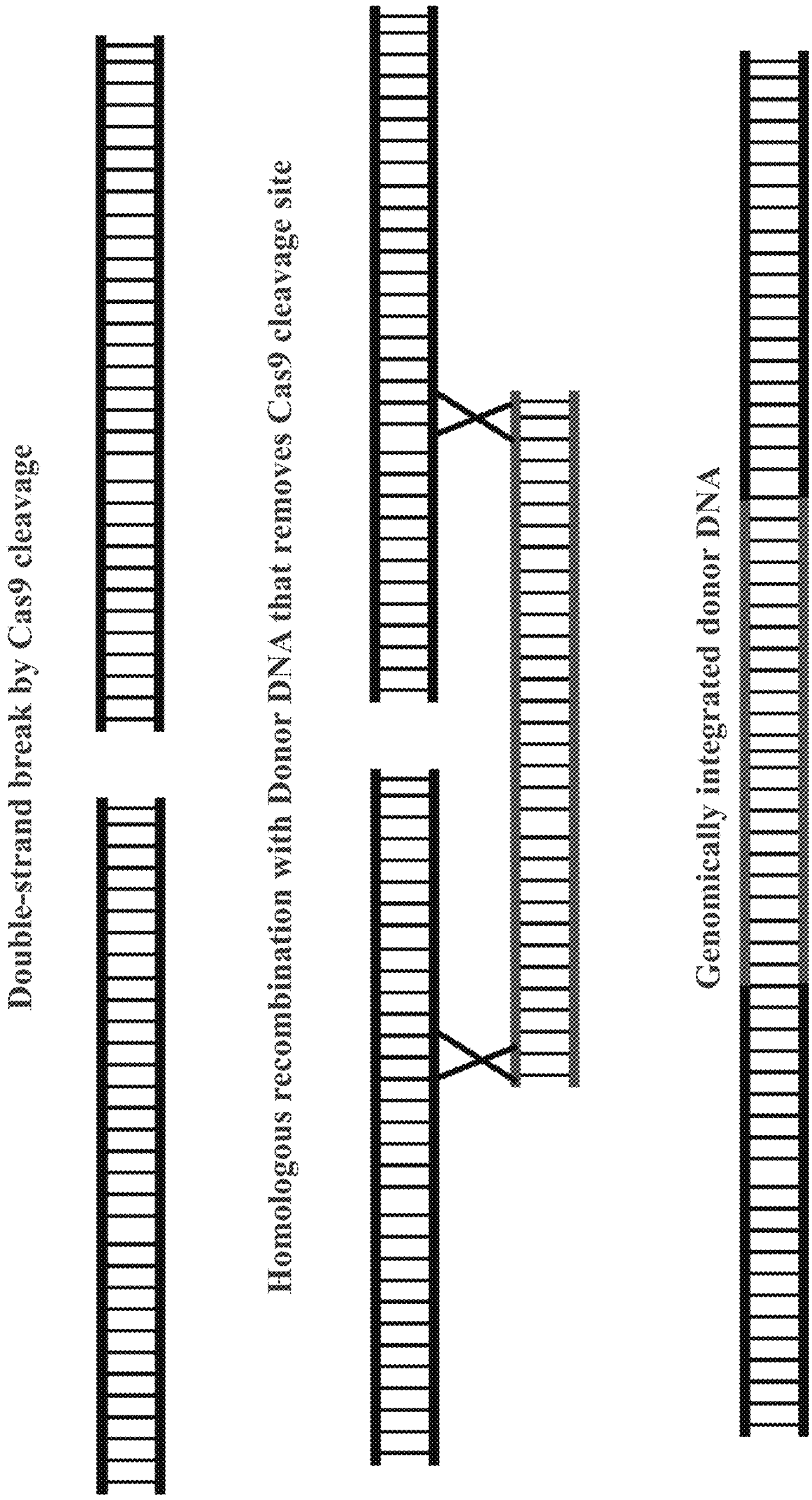

Embodiments of the present disclosure are based on the repeated use of exogenous DNA, nuclease enzymes such as DNA binding proteins and guide RNAs to co-localize to DNA and digest or cut the DNA with insertion of the exogenous DNA, such as by homologous recombination. Such DNA binding proteins are readily known to those of skill in the art to bind to DNA for various purposes. Such DNA binding proteins may be naturally occurring. DNA binding proteins included within the scope of the present disclosure include those which may be guided by RNA, referred to herein as guide RNA. According to this aspect, the guide RNA and the RNA guided DNA binding protein form a co-localization complex at the DNA. Such DNA binding proteins having nuclease activity are known to those of skill in the art, and include naturally occurring DNA binding proteins having nuclease activity, such as Cas9 proteins present, for example, in Type II CRISPR systems. Such Cas9 proteins and Type II CRISPR systems are well documented in the art. See Makarova et al., Nature Reviews, Microbiology, Vol. 9, June 2011, pp. 467-477 including all supplementary information hereby incorporated by reference in its entirety.

Exemplary DNA binding proteins having nuclease activity function to nick or cut double stranded DNA. Such nuclease activity may result from the DNA binding protein having one or more polypeptide sequences exhibiting nuclease activity. Such exemplary DNA binding proteins may have two separate nuclease domains with each domain responsible for cutting or nicking a particular strand of the double stranded DNA. Exemplary polypeptide sequences having nuclease activity known to those of skill in the art include the McrA-HNH nuclease related domain and the RuvC-like nuclease domain. Accordingly, exemplary DNA binding proteins are those that in nature contain one or more of the McrA-HNH nuclease related domain and the RuvC-like nuclease domain.

An exemplary DNA binding protein is an RNA guided DNA binding protein of a Type II CRISPR System. An exemplary DNA binding protein is a Cas9 protein.

In *S. pyogenes*, Cas9 generates a blunt-ended double-stranded break 3 bp upstream of the protospacer-adjacent motif (PAM) via a process mediated by two catalytic domains in the protein: an HNH domain that cleaves the complementary strand of the DNA and a RuvC-like domain that cleaves the non-complementary strand. See Jinke et al., Science 337, 816-821 (2012) hereby incorporated by reference in its entirety. Cas9 proteins are known to exist in many Type II CRISPR systems including the following as identified in the supplementary information to Makarova et al., Nature Reviews, Microbiology, Vol. 9, June 2011, pp. 467-477*: Methanococcus maripaludis* C7; *Corynebacterium diphtheriae; Corynebacterium efficiens* YS-314; *Corynebacterium glutamicum* ATCC 13032 Kitasato; *Corynebacterium glutamicum* ATCC 13032 Bielefeld; *Corynebacterium glutamicum* R; *Corynebacterium kroppenstedtii* DSM 44385; *Mycobacterium abscessus* ATCC 19977; *Nocardia farcinica* IFM10152; *Rhodococcus erythropolis* PR4; *Rhodococcus jostii* RHA1*; Rhodococcus opacus* B4 uid36573*; Acidothermus cellulolyticus* 11B; *Arthrobacter chlorophenolicus* A6; *Kribbella flavida* DSM 17836 uid43465*; Thermomonospora curvata* DSM 43183; *Bifidobacterium dentium* Bd1*; Bifidobacterium longum* DJO10A; *Slackia heliotrinireducens* DSM 20476*; Persephonella marina* EX H1; *Bacteroides fragilis* NCTC 9434*; Capnocytophaga ochracea* DSM 7271; *Flavobacterium psychrophilum* JIP02 86*; Akkermansia muciniphila* ATCC BAA 835*; Roseiflexus castenholzii* DSM 13941*; Roseiflexus* RS1; *Synechocystis* PCC6803*; Elusimicrobium minutum* Pei191; uncultured Termite group 1 bacterium phylotype Rs D17*; Fibrobacter succinogenes* S85; *Bacillus cereus* ATCC 10987; *Listeria innocua; Lactobacillus casei; Lactobacillus rhamnosus* GG; *Lactobacillus salivarius* UCC118; *Streptococcus agalactiae* A909; *Streptococcus agalactiae* NEM316; *Streptococcus agalactiae* 2603; *Streptococcus dysgalactiae equisimilis* GGS 124; *Streptococcus equi zooepidemicus* MGCS10565; *Streptococcus gallolyticus* UCN34 uid46061; *Streptococcus gordonii* Challis subst CH1; *Streptococcus mutans* NN2025 uid46353; *Streptococcus mutans; Streptococcus pyogenes* M1 GAS; *Streptococcus pyogenes* MGAS5005; *Streptococcus pyogenes* MGAS2096; *Streptococcus pyogenes* MGAS9429; *Streptococcus pyogenes* MGAS10270; *Streptococcus pyogenes* MGAS6180; *Streptococcus pyogenes* MGAS315; *Streptococcus pyogenes* SSI-1; *Streptococcus pyogenes* MGAS10750; *Streptococcus pyogenes* NZ131; *Streptococcus thermophiles* CNRZ1066; *Streptococcus thermophiles* LMD-9*; Streptococcus thermophiles* LMG 18311; *Clostridium botulinum* A3 Loch Maree; *Clostridium botulinum* B Eklund 17B; *Clostridium botulinum* Ba4 657; *Clostridium botulinum* F Langeland; *Clostridium cellulolyticum* H10; *Finegoldia magna* ATCC 29328; *Eubacterium rectale* ATCC 33656; *Mycoplasma gallisepticum; Mycoplasma mobile* 163K; *Mycoplasma penetrans; Mycoplasma synoviae* 53; *Streptobacillus moniliformis* DSM 12112; *Bradyrhizobium* BTAi1*; Nitrobacter hamburgensis* X14*; Rhodopseudomonas palustris* BisB18; *Rhodopseudomonas palustris* BisB5*; Parvibaculum lavamentivorans* DS-1*; Dinoroseobacter shibae* DFL 12; *Gluconacetobacter diazotrophicus* Pal 5 FAPERJ; *Gluconacetobacter diazotrophicus* Pal 5 JGI; *Azospirillum* B510 uid46085; *Rhodospirillum rubrum* ATCC 11170*; Diaphorobacter* TPSY uid29975*; Verminephrobacter eiseniae* EF01-2; *Neisseria meningitides* 053442; *Neisseria meningitides* alpha14; *Neisseria meningitides* Z2491; *Desulfovibrio salexigens* DSM 2638; *Campylobacter jejuni* doylei 269 97; *Campylobacter jejuni* 81116; *Campylobacter jejuni; Campylobacter lari* RM2100; *Helicobacter hepaticus; Wolinella succinogenes; Tolumonas auensis* DSM 9187; *Pseudoalteromonas atlantica* T6c; *Shewanella pealeana* ATCC 700345; *Legionella pneumophila* Paris; *Actinobacillus succinogenes* 130Z; *Pasteurella multocida; Francisella tularensis novicida* U112; *Francisella tularensis* holarctica; *Francisella tularensis* FSC 198; *Francisella tularensis tularensis; Francisella tularensis* WY96-3418; and *Treponema denticola* ATCC 35405. Accordingly, aspects of the present disclosure are directed to a Cas9 protein present in a Type II CRISPR system.

The Cas9 protein may be referred by one of skill in the art in the literature as Csn1. The *S. pyogenes* Cas9 protein sequence that is the subject of experiments described herein is shown below. See Deltcheva et al., Nature 471, 602-607 (2011) hereby incorporated by reference in its entirety.

```
                                        (SEQ ID NO: 2)
MDKKYSIGLDIGTNSVGWAVITDEYKVPSKKFKVLGNTDRHSIKKNLIG

ALLFDSGETAEATRLKRTARRRYTRRKNRICYLQEIFSNEMAKVDDSFF

HRLEESFLVEEDKKHERHPIFGNIVDEVAYHEKYPTIYHLRKKLVDSTD

KADLRLIYLALAHMIKFRGHFLIEGDLNPDNSDVDKLFIQLVQTYNQLF

EENPINASGVDAKAILSARLSKSRRLENLIAQLPGEKKNGLFGNLIALS

LGLTPNFKSNFDLAEDAKLQLSKDTYDDDLDNLLAQIGDQYADLFLAAK

NLSDAILLSDILRVNTEITKAPLSASMIKRYDEHHQDLTLLKALVRQQL

PEKYKEIFFDQSKNGYAGYIDGGASQEEFYKFIKPILEKMDGTEELLVK

LNREDLLRKQRTFDNGSIPHQIHLGELHAILRRQEDFYPFLKDNREKIE

KILTFRIPYYVGPLARGNSRFAWMTRKSEETITPWNFEEVVDKGASAQS

FIERMTNFDKNLPNEKVLPKHSLLYEYFTVYNELTKVKYVTEGMRKPAF

LSGEQKKAIVDLLFKTNRKVTVKQLKEDYFKKIECFDSVEISGVEDRFN

ASLGTYHDLLKIIKDKDFLDNEENEDILEDIVLTLTLFEDREMIEERLK

TYAHLFDDKVMKQLKRRRYTGWGRLSRKLINGIRDKQSGKTILDFLKSD

GFANRNFMQLIHDDSLTFKEDIQKAQVSGQGDSLHEHIANLAGSPAIKK

GILQTVKVVDELVKVMGRHKPENIVIEMARENQTTQKGQKNSRERMKRI

EEGIKELGSQILKEHPVENTQLQNEKLYLYYLQNGRDMYVDQELDINRL

SDYDVDHIVPQSFLKDDSIDNKVLTRSDKNRGKSDNVPSEEVVKKMKNY

WRQLLNAKLITQRKFDNLTKAERGGLSELDKAGFIKRQLVETRQITKHV

AQILDSRMNTKYDENDKLIREVKVITLKSKLVSDFRKDFQFYKVREINN

YHHAHDAYLNAVVGTALIKKYPKLESEFVYGDYKVYDVRKMIAKSEQEI

GKATAKYFFYSNIMNFFKTEITLANGEIRKRPLIETNGETGEIVWDKGR

DFATVRKVLSMPQVNIVKKTEVQTGGFSKESILPKRNSDKLIARKKDWD

PKKYGGFDSPTVAYSVLVVAKVEKGKSKKLKSVKELLGITIMERSSFEK

NPIDFLEAKGYKEVKKDLIIKLPKYSLFELENGRKRMLASAGELQKGNE

LALPSKYVNFLYLASHYEKLKGSPEDNEQKQLFVEQHKHYLDEIIEQIS

EFSKRVILADANLDKVLSAYNKHRDKPIREQAENIIHLFTLTNLGAPAA

FKYFDTTIDRKRYTSTKEVLDATLIHQSITGLYETRIDLSQLGGD-
```

According to one aspect, the RNA guided DNA binding protein includes homologs and orthologs of Cas9 which retain the ability of the protein to bind to the DNA, be guided by the RNA and cut the DNA. According to one aspect, the Cas9 protein includes the sequence as set forth for naturally occurring Cas9 from *S. pyogenes* and protein sequences having at least 30%, 40%, 50%, 60%, 70%, 80%, 90%, 95%, 98% or 99% homology thereto and being a DNA binding protein, such as an RNA guided DNA binding protein.

According to one aspect, an engineered Cas9-gRNA system is provided which enables RNA-guided genome cutting in a site specific manner, if desired, and modification of the genome by insertion of exogenous donor nucleic acids. The guide RNAs are complementary to target sites or target loci on the DNA. The guide RNAs can be crRNA-tracrRNA chimeras. The Cas9 binds at or near target genomic DNA. The one or more guide RNAs bind at or near target genomic DNA. The Cas9 cuts the target genomic DNA and exogenous donor DNA is inserted into the DNA at the cut site.

Accordingly, methods are directed to the use of a guide RNA with a Cas9 protein and an exogenous donor nucleic acid to multiplex insertions of exogenous donor nucleic acids into DNA within a cell expressing Cas9 by cycling the insertion of nucleic acid encoding the RNA and exogenous donor nucleic acid, expressing the RNA, colocalizing the RNA, Cas9 and DNA in a manner to cut the DNA, and insertion of the exogenous donor nucleic acid. The method steps can be cycled in any desired number to result in any desired number of DNA modifications. Methods of the present disclosure are accordingly directed to editing target genes using the Cas9 proteins and guide RNAs described herein to provide multiplex genetic and epigenetic engineering of cells.

Further aspects of the present disclosure are directed to the use of DNA binding proteins or systems in general for the multiplex insertion of exogenous donor nucleic acids into the DNA, such as genomic DNA, of a cell, such as a human cell. One of skill in the art will readily identify exemplary DNA binding systems based on the present disclosure.

Cells according to the present disclosure include any cell into which foreign nucleic acids can be introduced and expressed as described herein. It is to be understood that the basic concepts of the present disclosure described herein are not limited by cell type. Cells according to the present disclosure include eukaryotic cells, prokaryotic cells, animal cells, plant cells, fungal cells, archael cells, eubacterial cells and the like. Cells include eukaryotic cells such as yeast cells, plant cells, and animal cells. Particular cells include mammalian cells, such as human cells. Further, cells include any in which it would be beneficial or desirable to modify DNA.

Target nucleic acids include any nucleic acid sequence to which a co-localization complex as described herein can be useful to nick or cut. Target nucleic acids include genes. For purposes of the present disclosure, DNA, such as double stranded DNA, can include the target nucleic acid and a co-localization complex can bind to or otherwise co-localize with the DNA at or adjacent or near the target nucleic acid and in a manner in which the co-localization complex may have a desired effect on the target nucleic acid. Such target nucleic acids can include endogenous (or naturally occurring) nucleic acids and exogenous (or foreign) nucleic acids. One of skill based on the present disclosure will readily be able to identify or design guide RNAs and Cas9 proteins which co-localize to a DNA including a target nucleic acid. One of skill will further be able to identify transcriptional regulator proteins or domains which likewise co-localize to a DNA including a target nucleic acid. DNA includes genomic DNA, mitochondrial DNA, viral DNA or exogenous DNA. According to one aspect, materials and methods useful in the practice of the present disclosure include those described in Di Carlo, et al., Nucleic Acids Research, 2013, vol. 41, No. 7 4336-4343 hereby incorporated by reference in its entirety for all purposes including exemplary strains and media, plasmid construction, transformation of plasmids, electroporation of transcient gRNA cassette and donor nucleic acids, transformation of gRNA plasmid with donor DNA into Cas9-expressing cells, galactose induction of Cas9, identification of CRISPR-Cas targets in yeast genome, etc. Additional references including information, materials and methods useful to one of skill in carrying out the invention are provided in Mali, P., Yang, L., Esvelt, K. M., Aach, J., Guell, M., DiCarlo, J. E., Norville, J. E. and Church, G M. (2013) RNA-Guided human genome engineering via Cas9. Science, 10.1126fscience.1232033; Storici, F., Durham, C. L., Gordenin, D. A. and Resnick, M. A. (2003) Chromosomal site-specific double-strand breaks are efficiently targeted for repair by oligonucleotides in yeast. PNAS, 100, 14994-14999 and Jinek, M., Chylinski, K., Fonfara, 1., Hauer, M., Doudna, J. A. and Charpentier, E. (2012) A programmable dual-RNA-Guided DNA endonuclease in adaptive bacterial immunity. Science, 337, 816-821 each of which are hereby incorporated by reference in their entireties for all purposes.

Foreign nucleic acids (i.e. those which are not part of a cell's natural nucleic acid composition) may be introduced into a cell using any method known to those skilled in the art for such introduction. Such methods include transfection, transduction, viral transduction, microinjection, lipofection, nucleofection, nanoparticle bombardment, transformation, conjugation and the like. One of skill in the art will readily understand and adapt such methods using readily identifiable literature sources.

The following examples are set forth as being representative of the present disclosure. These examples are not to be construed as limiting the scope of the present disclosure as these and other equivalent embodiments will be apparent in view of the present disclosure, figures and accompanying claims.

Example I

General Process for Multiplexed Gene Editing Using CRISPR-Cas9 in Yeast

Cas9 from the CRISPR immune system of *Streptococcous pyogenes* is used to stimulate homologous recombination and to select against cells that do not recombine transformed DNA in *Saccharomyces cerevisiae*. A general method of RNA-guided DNA cleavage using Cas9 is presented in FIG. 1. A co-localization complex is formed between Cas9, a guide RNA and the target DNA. A double stranded break is created in the target DNA by Cas9. Donor DNA is then inserted into the DNA by homologous recombination. The donor DNA includes flanking sequences on either side of the cut site and a sequence that removes the Cas9 cleavage site. The result is integration of the donor DNA into the DNA, which may be genomic DNA.

Figure 2:
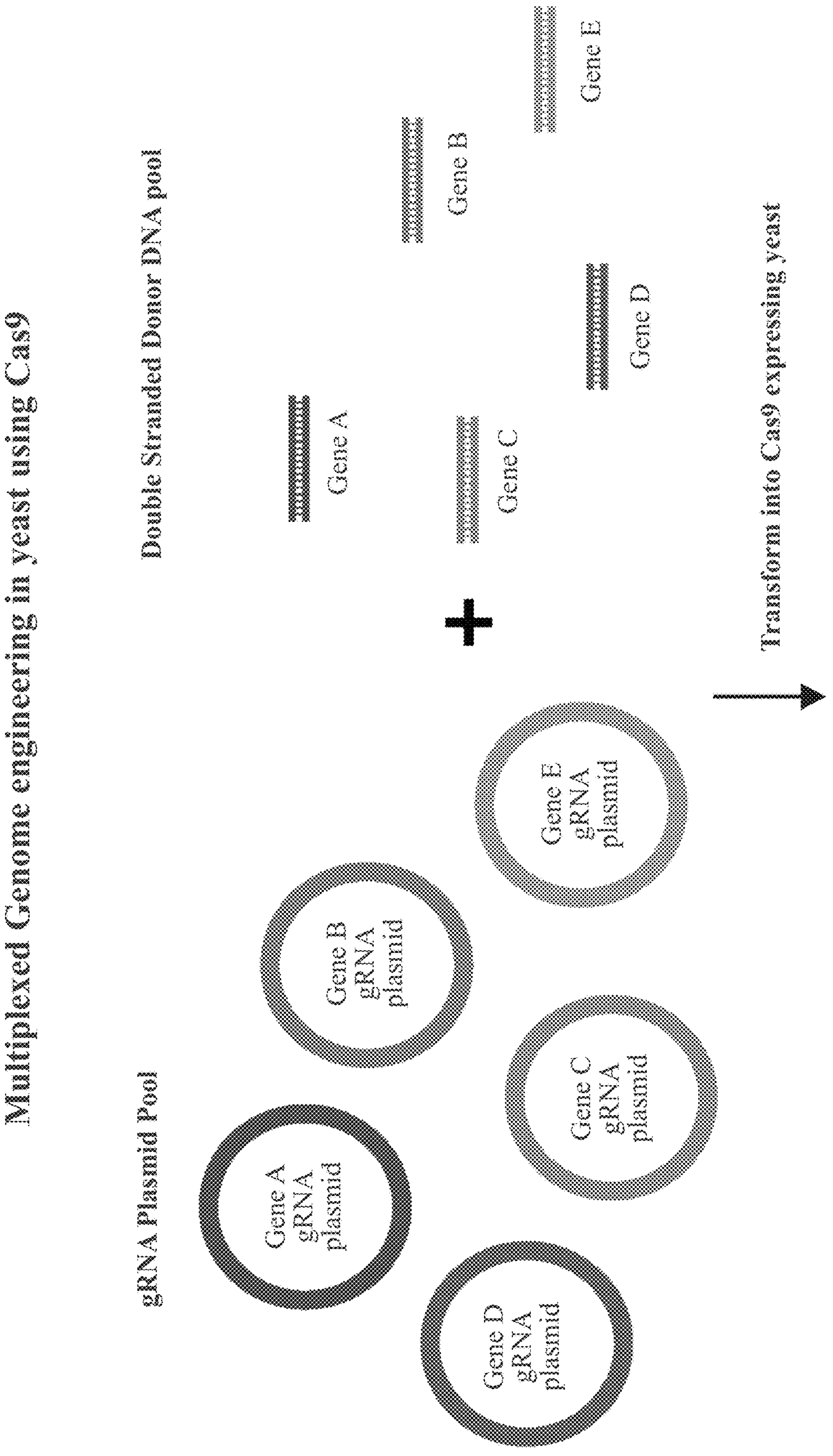
FIG. 2 is a schematic depicting multiplexed genome engineering in yeast using Cas9.
Figure 2:
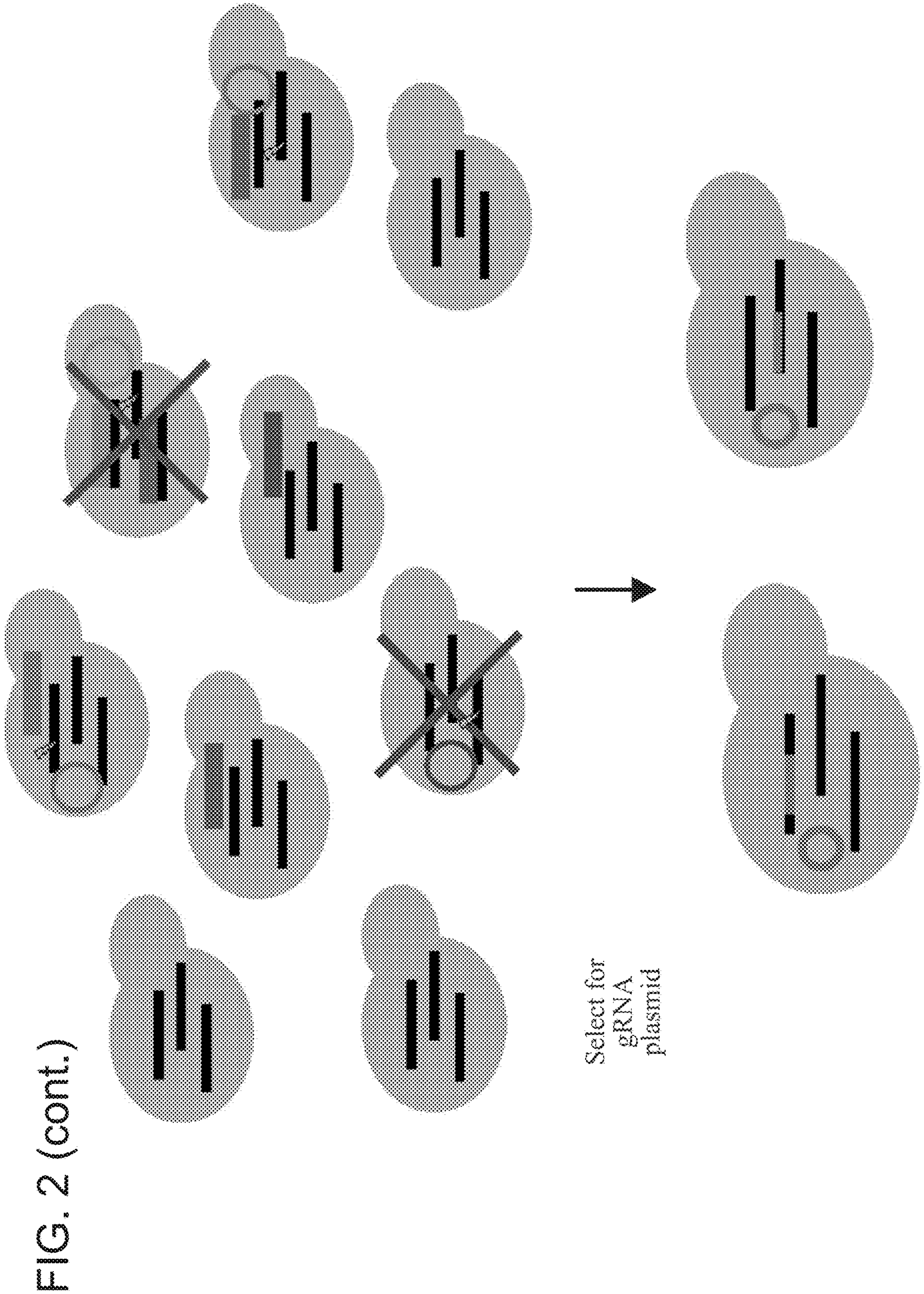

A general method for high frequency donor DNA recombination using multiplexed DNA engineering in yeast using Cas9 is provided as follows and with reference to FIG. 2. Cells not having a naturally present Cas9 RNA guided endonuclease may be transformed with DNA to allow the cell to express a Cas9 RNA guided endonuclease. Cells are grown that express a Cas9 RNA-guided endonuclease. A plasmid including one or more nucleic acids encoding one or more guide RNAs and a selection marker known to those of skill in the art is created for introduction into a cell and expression of the one or more guide RNAs. As shown in FIG. 2, a pool of plasmids is shown each with a nucleic acid encoding a guide RNA to be used for a different gene to be inserted into the genomic DNA of the cell, i.e. gene A, gene B, gene C, gene D and gene E. A pool of donor DNA is also provided including double stranded donor DNA for gene A, gene B, gene C, gene D and gene E.

Cells are washed and conditioned with lithium acetate. Cells may be further washed and mixed with a pool of exogenous donor nucleic acids, such as double stranded oligonucleotides, for example a DNA cassette, and the plasmids including the nucleic acids encoding the guide RNAs. As shown in FIG. 2, the cells are transformed with the exogenous donor nucleic acids and the plasmids using PEG 3350 and lithium acetate.

As shown in FIG. 2, cells are selected for the one or more guide RNAs using the selection marker. The selected cells express the one or more guide RNAs. One or more co-localization complexes are formed between a guide RNA, a Cas9 RNA-guided endonuclease and DNA in the cell. The endonuclease cuts the DNA and a donor nucleic acid is inserted into the cell by recombination, such as homologous recombination. The cells are then cured for the plasmid and the cells are then optionally subjected to one or additional cycles of the above steps. A plurality of cycles may be performed. A cell subjected to a plurality of cycles exhibits high recombination frequency. Alternatively, the cells are deselected for plasmid maintenance or otherwise the cells are placed in media to select against cells with the plasmid. The process is then repeated beginning with the cell growth step. Accordingly, methods include cycling of cells already modified by a prior cycle or selecting cells from a prior cycle which have not been modified and further cycling the unmodified cells to effect modification of DNA as described herein.

Example II

Detailed Cycling Protocol

Cells are grown (uracil auxotrophs, with constitutive Cas9 expression) to an optical density of 0.8 to 1.0 in 5 ml SC yeast media or of SC+FOA (100 μg/ml). The cells are spun at 2250×g for 3 minutes, and are washed once with 10 ml water. the cells are sun and resuspended in 1 ml of 100 mM lithium acetate. The cells are pelleted and resuspended in 500 μl 100 mM lithium acetate. A transformation mixture is created by adding in the following order, 50 μl of cells; DNA mixture including 1 nmol of double stranded oligonucleotide pool, 5 μg each of guide RNA (p426 vector, with uracil marker) and fill to 70 μl with water to achieve desired final volume; 240 μl 50% PEG 3350; and 36 μM lithium acetate. The mixture is incubated at 30° C. for 30 minutes. The mixture is then vortexed and the cells are heat shocked by incubating the mixture at 42° C. for 20 minutes. The cells are then pelleted and the supernatant is removed. The cells are inoculated with 5 ml SC-uracil to select for uracil gene containing gRNA plasmid. The cells are allowed to recover for 2 days. After two days, 100 μl of the cell culture is inoculated into 5 ml fresh SC and allowed to grow for 12 hours to deselect for plasmid maintenance. 100 μl of the SC culture cells are then inoculated into 5 ml of SC+FOA (100 μg/mL) media to select against cells with the plasmid. This completes one cycle of the process. The process is repeated for any number of desired cycles. The total process may include 1 cycle, 2 cycles, 3 cycles, 4 cycles, 5 cycles, 6 cycles, 7 cycles, 8 cycles, 9 cycles, 10 cycles, 15 cycles, 20, cycles, 25 cycles, etc.

Example III

Thermotolerance to Heat Shock in Select Mutants

Using the methods described herein, thermotolerance to heat shock in select mutants has been shown. Genes that have been shown to increase thermotolerance in yeast upon knockout or point mutation were targeted by the guide RNA-Cas9 system described herein. Four genes were selected for mutation: UBC1, SCH9, TFS1, and RAS2. SCH9 is a protein kinase that regulates osmostress, nutrient and environmental stress genes. TFS1 inhibits carboxypeptidase Y and Ira2p, inhibits Ras GAP activity and responds to DNA replicative stress. RAS2 is a GTP binding protein that regulates nitrogen starvation and is involved in stress response pathways. For each of SCH9, TFS1 and RAS2, a donor DNA was created which is an allele containing a serine to alanine mutation in the coding region. UBC1-E2 is a ubiquitin-conjugating enzyme. A donor DNA including a point mutation that removes a phosphorylation site resulting in thermotolerance was created.

Figure 3:
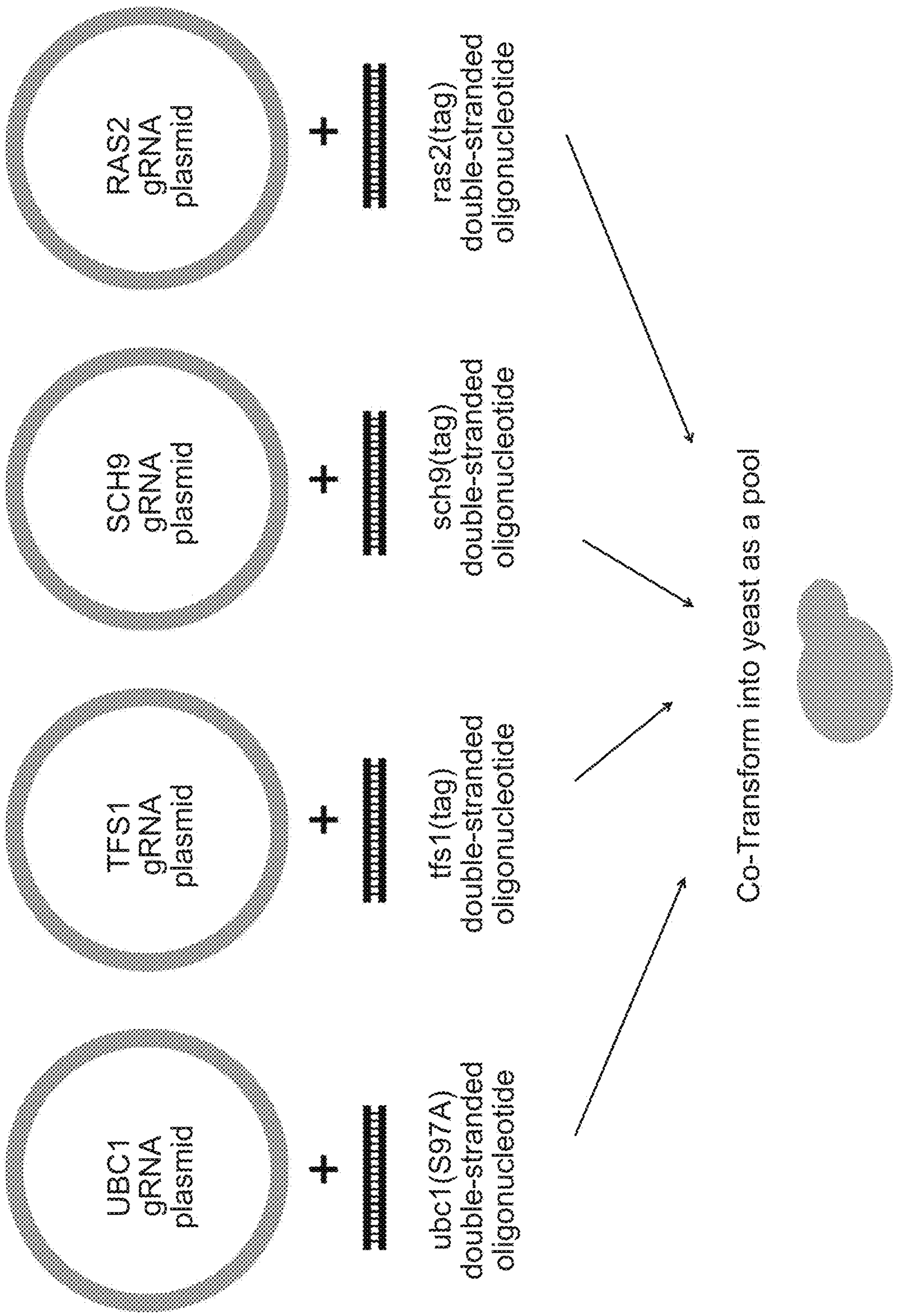
FIG. 3 is a schematic depicting allele replacement using oligonucleotides targeting four loci crucial in thermotolerance in yeast.
Figure 4:
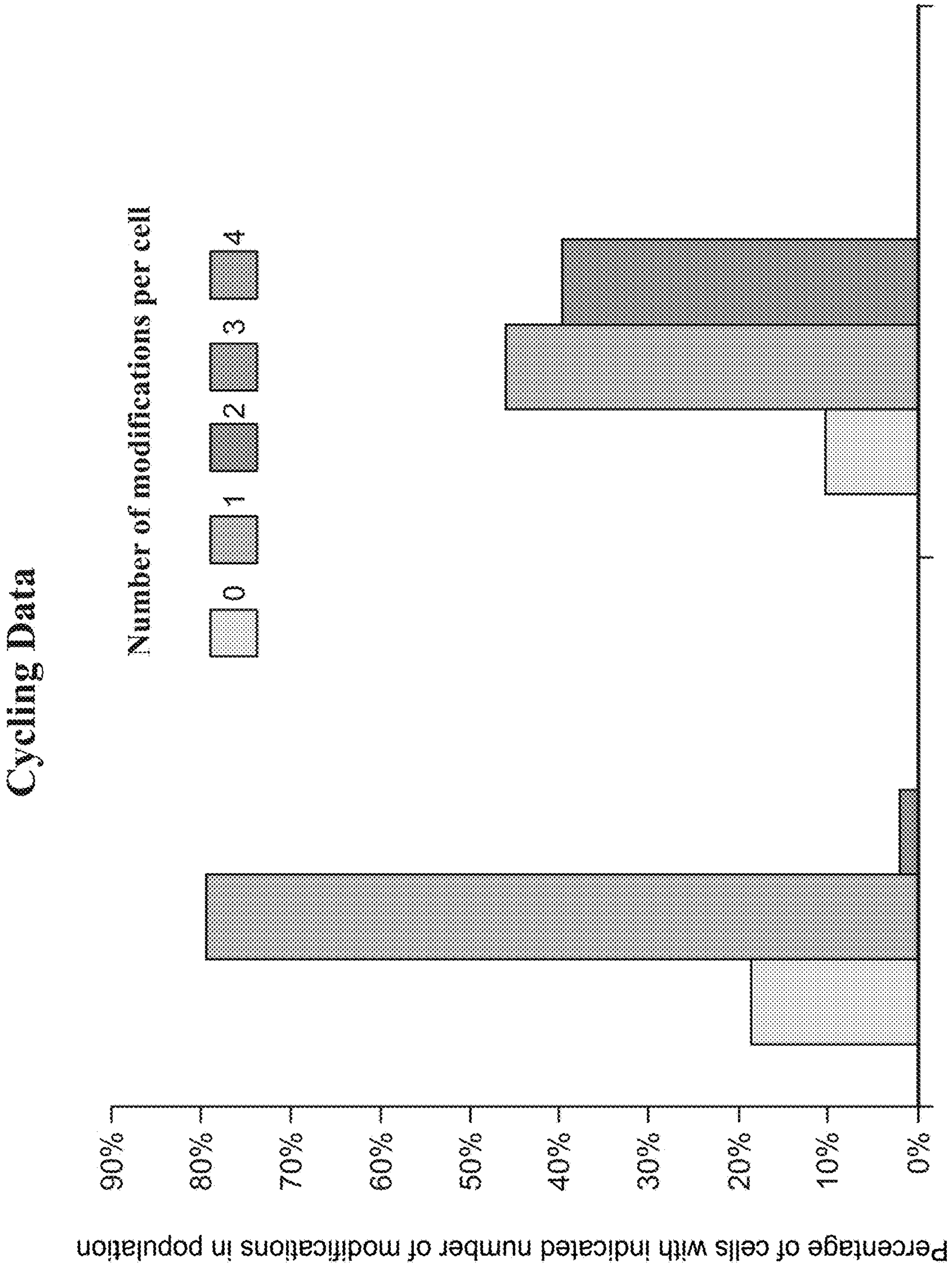
FIG. 4 is a graph depicting number of modifications per cell after one cycle and after two cycles.

Using the methods described herein the genes were targeted using guide RNA designed to direct Cas9 cleavage to the loci of the genes along with double stranded oligonucleotide to impart the changes. As shown in FIG. 3, allele replacement was achieved using oligonucleotides targeting four loci responsible for thermotolerance in yeast. According to the schematic, four plasmids each incorporating a nucleic acid encoding a guide RNA for one of the genes were created: UBC1 gRNS plasmid, TFS1 gRNA plasmid, SCH9 gRNA plasmid and RAS2 gRNA plasmid. Each plasmid had a corresponding double stranded donor oligonucleotide: ubc1 (S97A) double stranded oligonucleotide, tfs1 (tag) double stranded oligonucleotide, sch9 (tag) double stranded oligonucleotide and ras (tag) double stranded oligonucleotide. The plasmids and the corresponding double stranded donor oligonucleotides were co-transformed into yeast as a pool. Two cycles were performed and the number of modifications per cell as a function of percentage of cells in the cell population is shown at FIG. 4. A significant number of cells included one and two modifications after cycle 2. One triple mutant was able to be isolated (data not shown.)

Figure 5B:
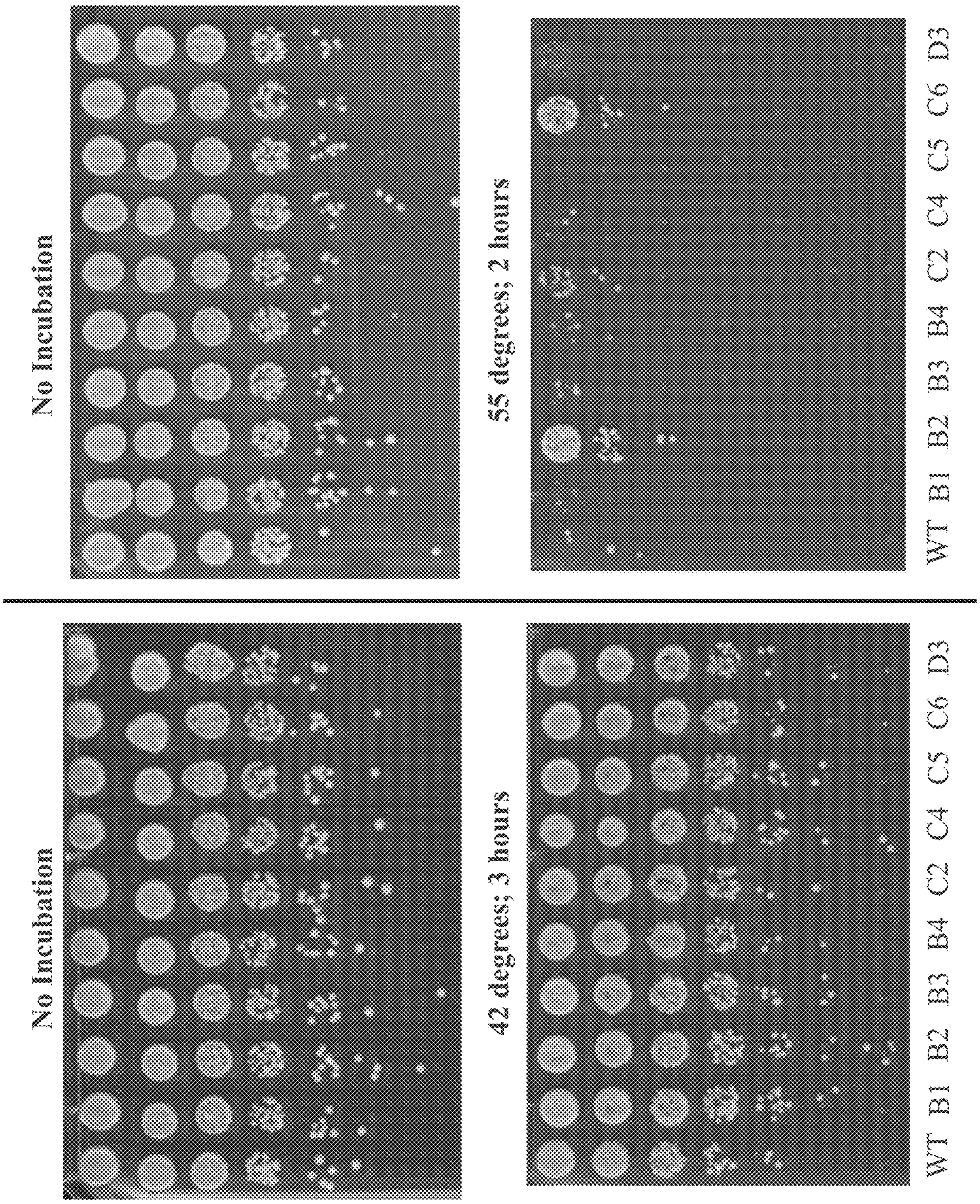
FIG. 5B shows thermotolerance to heat shock for the various strains.

FIG. 5A is a table of the strains resulting from the methods described herein showing strains transformed with one donor oligonucleotide, strains transformed with two donor oligonucleotides and a strain transformed with three donor oligonucleotides. FIG. 5B shows the effect of incubation at 42° C. for three hours compared to no incubation and s slight decrease in wild type cell number. FIG. 5B also shows the effect of incubation at 55° C. for two hours compared to no incubation. The mutants most tolerant to heat shock at 55° C. were sch9, sch9 tfs1 and tfs1 ubc1(s97a).

Figure 6A:
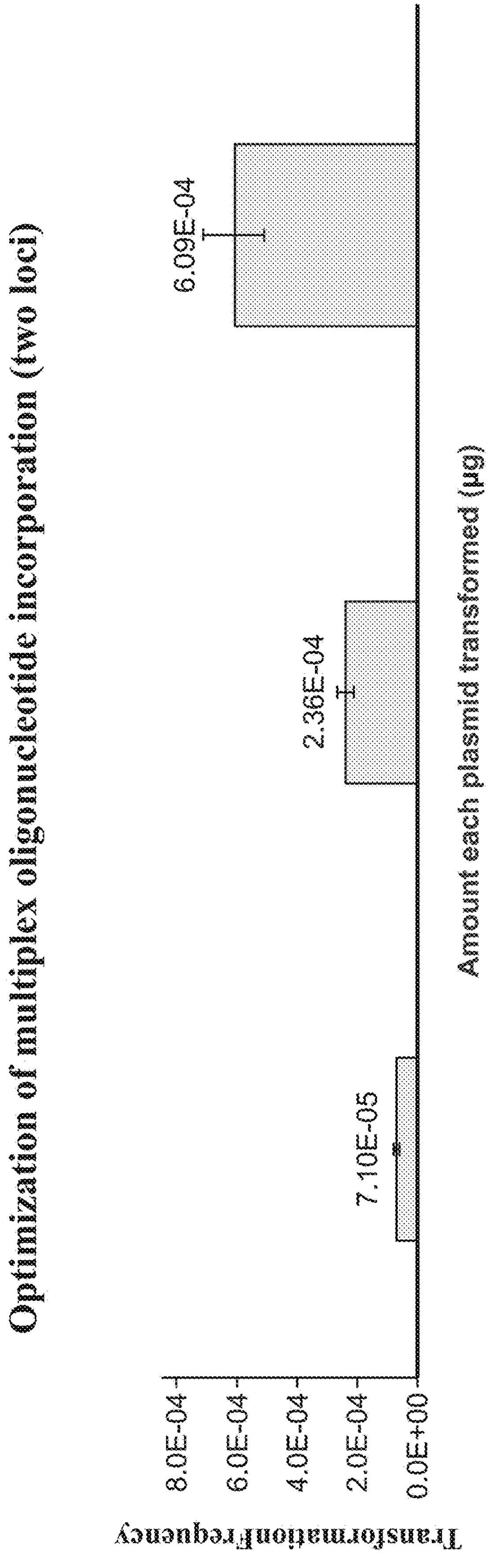
FIG. 6A depicts graphical data for transformation frequency.
Figures 6B, 6C:
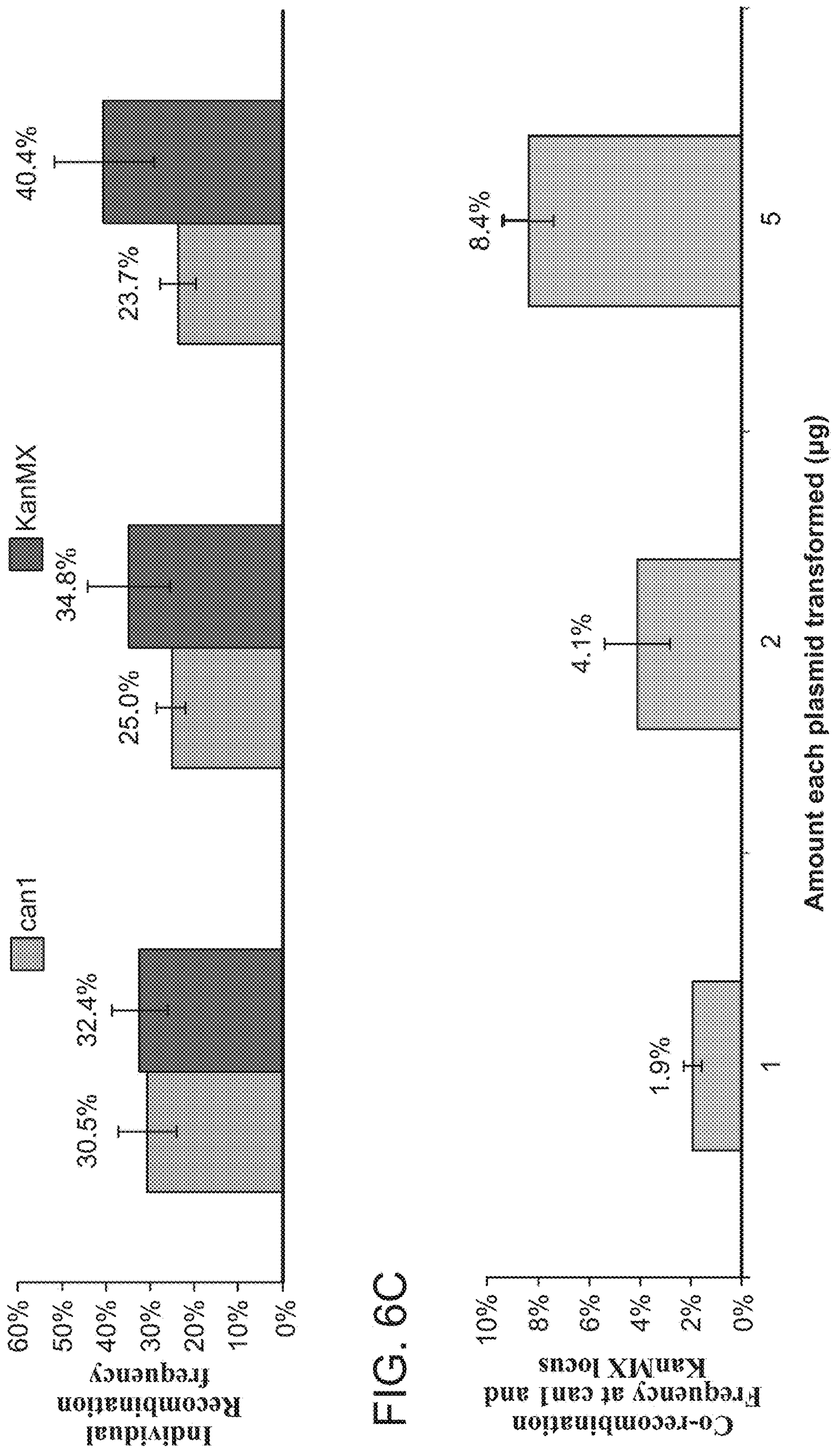
FIG. 6B depicts graphical data for individual recombination frequency.
FIG. 6C depicts graphical data for co-recombination frequency at can1 and KanMX locus.

FIG. 6 in general provides graphical information on the optimization of multiplex oligonucleotide incorporation for two loci. FIG. 6A depicts the transformation frequency versus the amount of each plasmid transformed (μg). FIG. 6B depicts the individual recombination frequency versus the amount of each plasmid transformed (μg). FIG. 6C depicts the co-recombination frequency at can1 and KanMX locus versus the amount of each plasmid transformed (μg).

Figure 7:
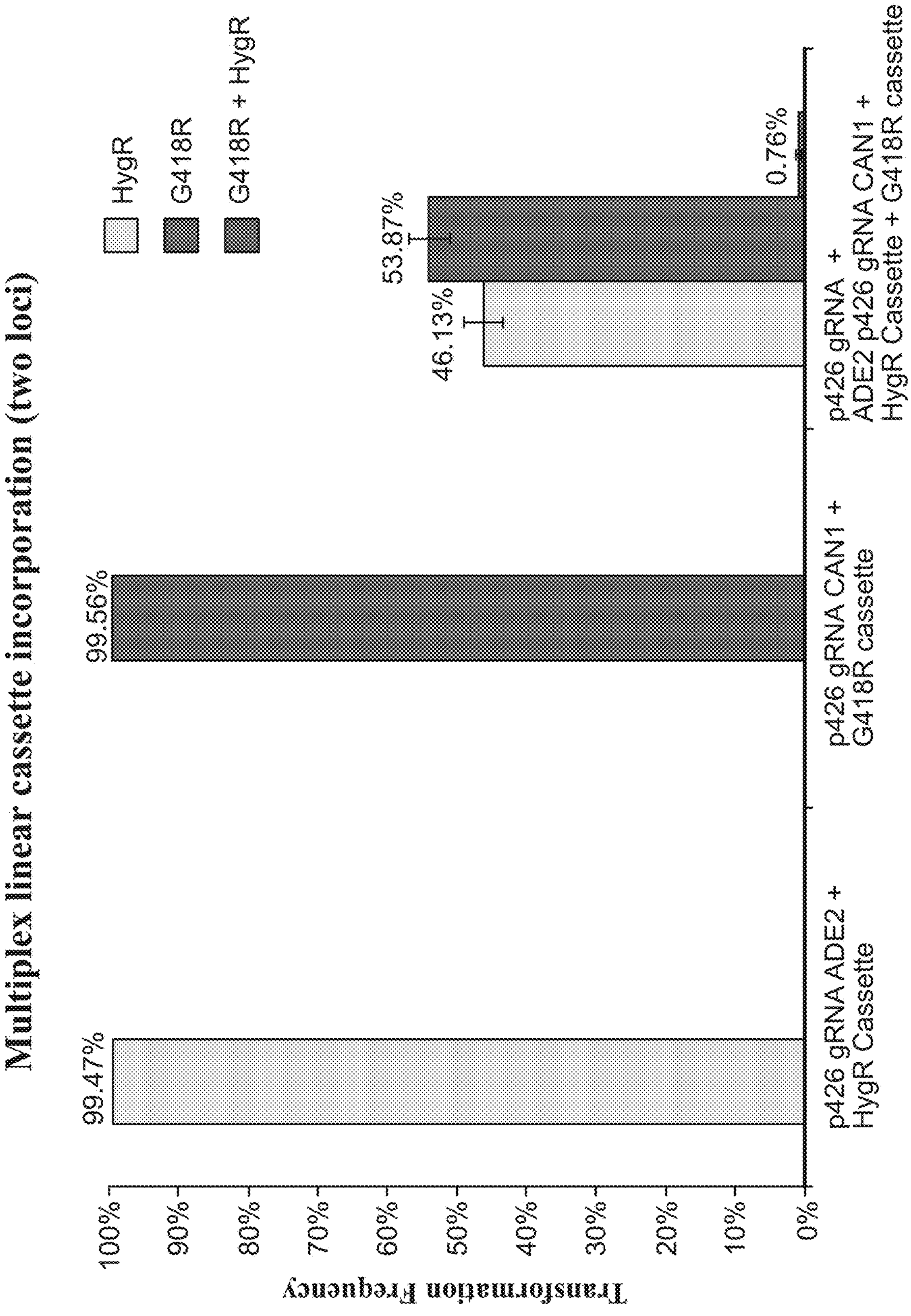
FIG. 7 depicts graphical data for multiplex linear cassette incorporation for two loci.
Figure 8A:
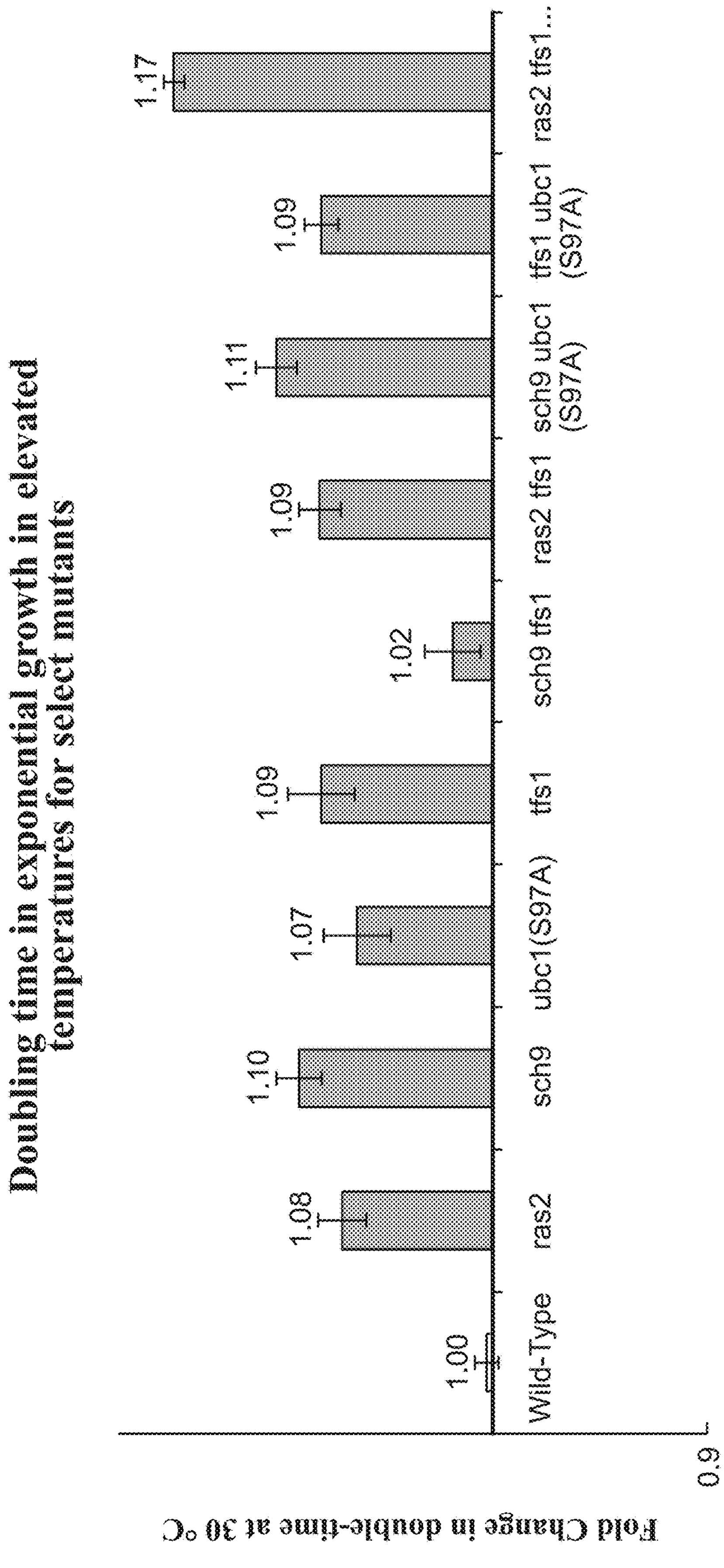
FIG. 8A depicts graphical data for fold change in double time at 30° C.
Figure 8B:
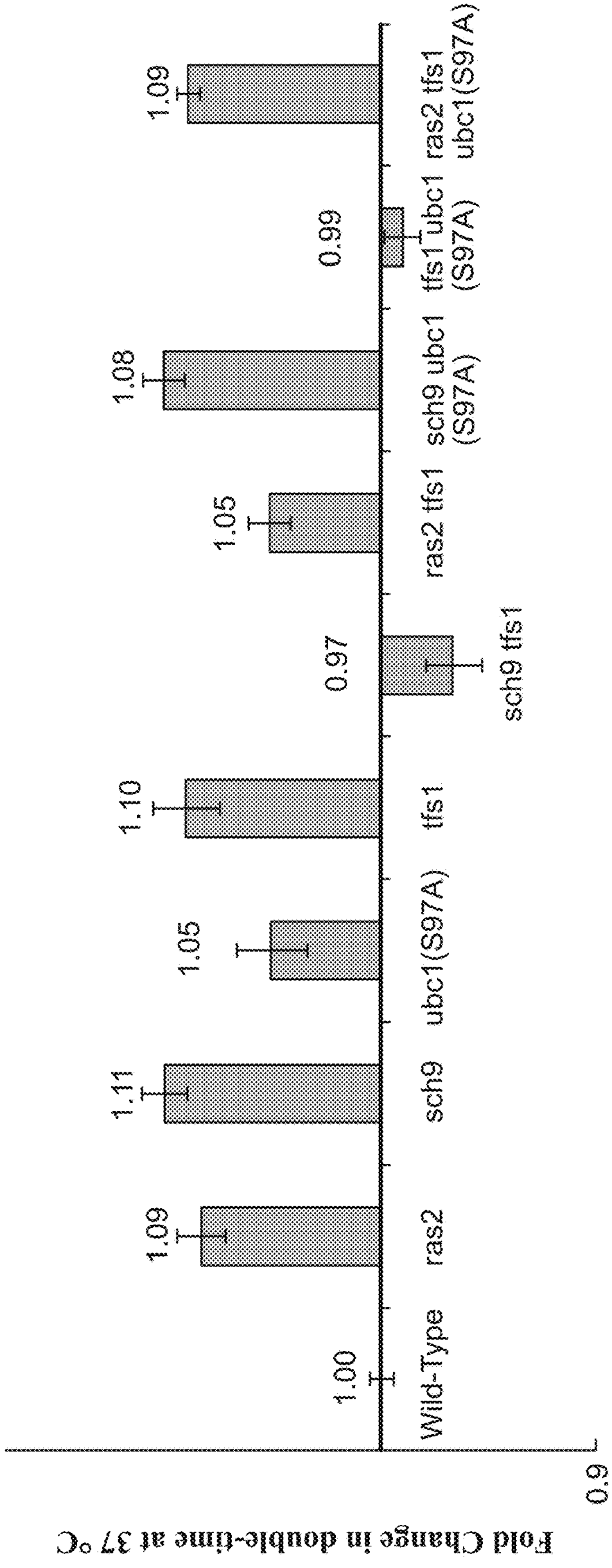
FIG. 8B depicts graphical data for fold change in double time at 37° C.
Figure 8C:
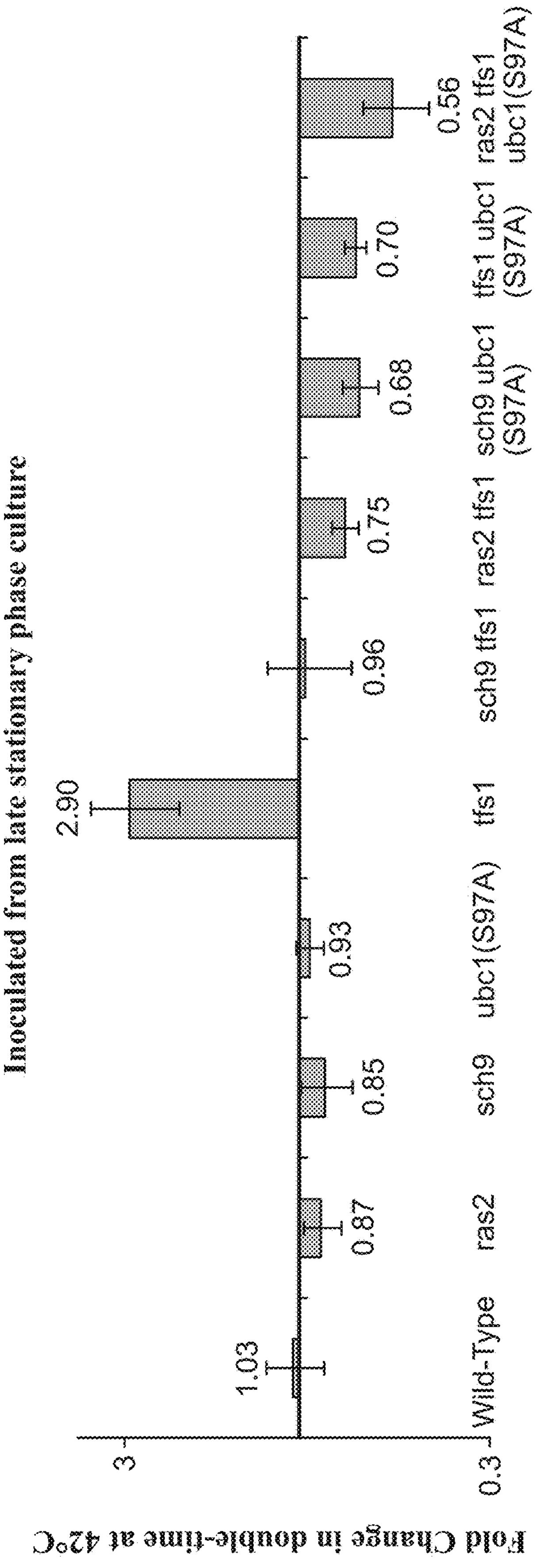
FIG. 8C depicts graphical data for fold change in double time at 42° C. with cells inoculated from the late stationary phase culture.
Figure 8D:
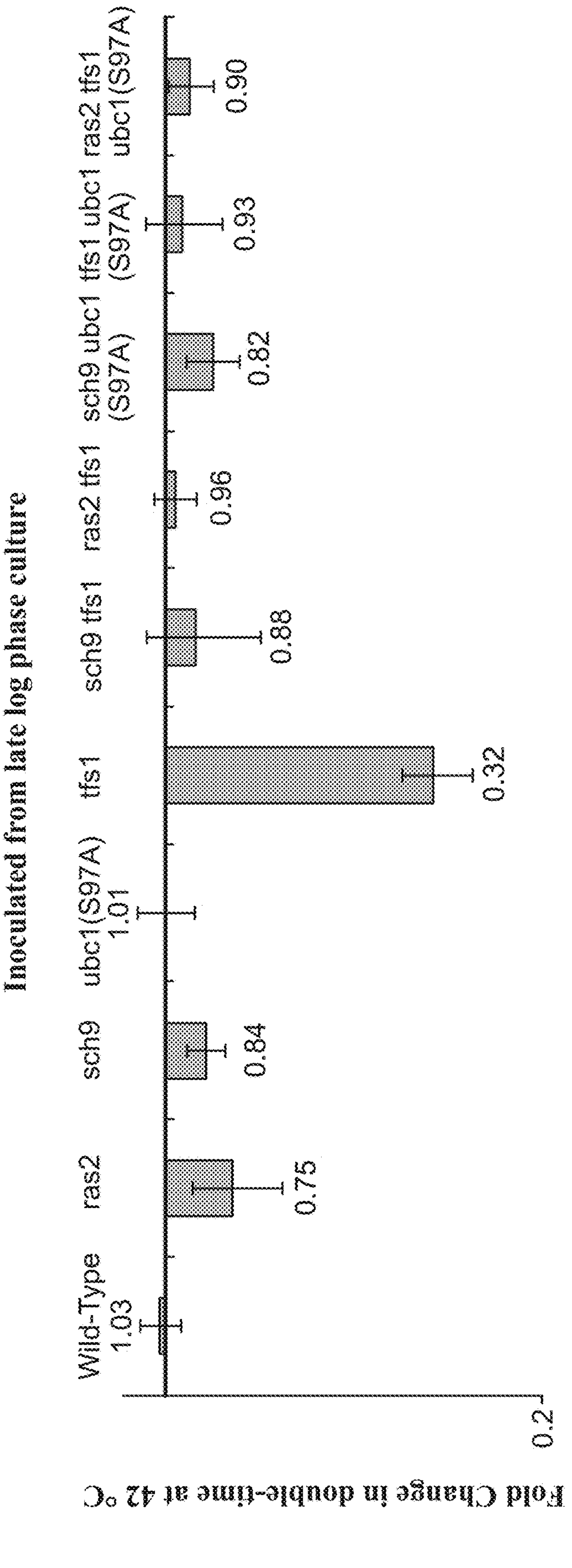
FIG. 8D depicts graphical data for fold change in double time at 42° C. with cells inoculated from the late log phase culture.

FIG. 7 in general provides graphical information on the multiplex linear cassette incorporation for two loci. The graph charts for the first left most bar, transformation frequency for p426 gRNA ADE2+HygR Cassette; for the next bar, transformation frequency for p426 gRNA CAN1+G418R cassette, for the next three bars, transformation frequency for p426 gRNA+ADE2 p426 gRNA CAN1+HygR Cassette+G418R cassette.

FIG. 8 in general is a growth rate analysis showing double time in exponential growth in elevated temperatures for select mutants. FIG. 8A graphs the fold change in double time at 30° C. for the wild type and the mutants identified. FIG. 8B graphs the fold change in double time at 37° C. for the wild type and the mutants identified. FIG. 8C graphs the fold change in double time at 42° C. for the wild type and the mutants identified as inoculated from the late stationary phase culture. FIG. 8D graphs the fold change in double time at 42° C. for the wild type and the mutants identified as inoculated from the late log phase culture. The graphical data shows a lower doubling time at 37° C. for sch9 tfs1 and tfs1 ubc1(S97A). The graphical data shows lower doubling time at 42° C. for ras2 tfs1, sch9 ubc1(S97A), tfs1 ubc1 (S97A) and ras2 tfs1 ubc1(S97A).

The invention claimed is:

1. An isolated cell expressing an RNA guided DNA binding protein of a Type II CRISPR system that forms a co-localization complex with guide RNA complementary to target DNA and that cleaves the target DNA in a site specific manner comprising (a) a plurality of guide RNAs complementary to different sites of DNA within the cell, and (b) a plurality of exogenous double-stranded donor nucleic acid sequences, wherein each exogenous double-stranded donor nucleic acid sequence of the plurality of exogenous double-stranded nucleic acid sequences includes homology sequences or arms flanking a cut site.

2. The cell of claim 1 wherein the cell comprises multiple exogenous double-stranded donor nucleic acid sequence insertions into the target DNA within the cell.

3. The cell of claim 1 wherein the RNA guided-DNA binding protein of a Type II CRISPR system is Cas9.

4. The cell of claim 1 wherein the cell is a eukaryotic cell.

5. The cell of claim 1 wherein the cell is a yeast cell, a plant cell or an animal cell.

6. The cell of claim 1 wherein each guide RNA of the plurality of guide RNAs is about 10 to about 500 nucleotides.

7. The cell of claim 1 wherein each guide RNA of the plurality of guide RNAs is about 20 to about 100 nucleotides.

8. The cell of claim 1 wherein each guide RNA of the plurality of guide RNAs is a tracrRNA-crRNA fusion.

9. The cell of claim 1 wherein the target DNA is genomic DNA, mitochondrial DNA, viral DNA, or exogenous DNA.

10. The cell of claim 1 wherein each guide RNA of the plurality of guide RNAs is encoded on a plasmid.

11. The cell of claim 1 wherein each guide RNA of the plurality of guide RNAs and each exogenous double-stranded donor nucleic acid sequence of the plurality of exogenous double-stranded donor acid sequences are encoded on a plasmid.

12. The cell of claim 1 wherein each exogenous double-stranded donor nucleic acid sequence of the plurality of exogenous double-stranded donor nucleic acid sequences further includes a sequence to remove a cut site.

13. The cell of claim 1 wherein the RNA guided-DNA binding protein of a Type II CRISPR system is *S. pyogenes* Cas9.

* * * * *

SEQUENCE LISTING

<160> NUMBER OF SEQ ID NOS: 2

<210> SEQ ID NO 1
<211> LENGTH: 110
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (1)..(20)
<223> OTHER INFORMATION: a, c, u, g, unknown or other

<400> SEQUENCE: 1
nnnnnnnnnn nnnnnnnnnn guuuuagagc uagaaauagc aaguuaaaau aaggcuaguc 60
cguuaucaac uugaaaaaag ugaguggcac cgagucggug gugcuuuuuu 110

<210> SEQ ID NO 2
<211> LENGTH: 1368
<212> TYPE: PRT
<213> ORGANISM: Streptococcus pyogenes

<400> SEQUENCE: 2

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270
```

-continued

```
Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685
```

```
Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                1005

Val Tyr  Gly Asp Tyr Lys Val  Tyr Asp Val Arg Lys  Met Ile Ala
    1010                1015                1020

Lys Ser  Glu Gln Glu Ile Gly  Lys Ala Thr Ala Lys  Tyr Phe Phe
    1025                1030                1035

Tyr Ser  Asn Ile Met Asn Phe  Phe Lys Thr Glu Ile  Thr Leu Ala
    1040                1045                1050

Asn Gly  Glu Ile Arg Lys Arg  Pro Leu Ile Glu Thr  Asn Gly Glu
    1055                1060                1065

Thr Gly  Glu Ile Val Trp Asp  Lys Gly Arg Asp Phe  Ala Thr Val
    1070                1075                1080

Arg Lys  Val Leu Ser Met Pro  Gln Val Asn Ile Val  Lys Lys Thr
    1085                1090                1095

Glu Val  Gln Thr Gly Gly Phe  Ser Lys Glu Ser Ile  Leu Pro Lys
```

-continued

```
    1100                1105                1110

Arg Asn  Ser Asp Lys Leu Ile  Ala Arg Lys Lys Asp  Trp Asp Pro
    1115                1120                1125

Lys Lys  Tyr Gly Gly Phe Asp  Ser Pro Thr Val Ala  Tyr Ser Val
    1130                1135                1140

Leu Val  Val Ala Lys Val Glu  Lys Gly Lys Ser Lys  Lys Leu Lys
    1145                1150                1155

Ser Val  Lys Glu Leu Leu Gly  Ile Thr Ile Met Glu  Arg Ser Ser
    1160                1165                1170

Phe Glu  Lys Asn Pro Ile Asp  Phe Leu Glu Ala Lys  Gly Tyr Lys
    1175                1180                1185

Glu Val  Lys Lys Asp Leu Ile  Ile Lys Leu Pro Lys  Tyr Ser Leu
    1190                1195                1200

Phe Glu  Leu Glu Asn Gly Arg  Lys Arg Met Leu Ala  Ser Ala Gly
    1205                1210                1215

Glu Leu  Gln Lys Gly Asn Glu  Leu Ala Leu Pro Ser  Lys Tyr Val
    1220                1225                1230

Asn Phe  Leu Tyr Leu Ala Ser  His Tyr Glu Lys Leu  Lys Gly Ser
    1235                1240                1245

Pro Glu  Asp Asn Glu Gln Lys  Gln Leu Phe Val Glu  Gln His Lys
    1250                1255                1260

His Tyr  Leu Asp Glu Ile Ile  Glu Gln Ile Ser Glu  Phe Ser Lys
    1265                1270                1275

Arg Val  Ile Leu Ala Asp Ala  Asn Leu Asp Lys Val  Leu Ser Ala
    1280                1285                1290

Tyr Asn  Lys His Arg Asp Lys  Pro Ile Arg Glu Gln  Ala Glu Asn
    1295                1300                1305

Ile Ile  His Leu Phe Thr Leu  Thr Asn Leu Gly Ala  Pro Ala Ala
    1310                1315                1320

Phe Lys  Tyr Phe Asp Thr Thr  Ile Asp Arg Lys Arg  Tyr Thr Ser
    1325                1330                1335

Thr Lys  Glu Val Leu Asp Ala  Thr Leu Ile His Gln  Ser Ile Thr
    1340                1345                1350

Gly Leu  Tyr Glu Thr Arg Ile  Asp Leu Ser Gln Leu  Gly Gly Asp
    1355                1360                1365
```